United States Patent
Hartwig et al.

(10) Patent No.: US 6,235,938 B1
(45) Date of Patent: May 22, 2001

(54) TRANSITION METAL-CATALYZED PROCESS FOR PREPARING N-ARYL AMINE COMPOUNDS

(75) Inventors: John F. Hartwig, New Haven, CT (US); Blake C. Hamann, Winchester, MA (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/329,474

(22) Filed: Jun. 10, 1999

(51) Int. Cl.[7] .................................................. C07C 209/00
(52) U.S. Cl. ............................................. 564/407; 564/405
(58) Field of Search ...................... 564/405, 407

(56) References Cited

U.S. PATENT DOCUMENTS 5,576,460   11/1996   Buchwald et al. .................... 564/386

FOREIGN PATENT DOCUMENTS

312253 * 4/1989 (EP).
538222 * 4/1993 (EP).

OTHER PUBLICATIONS

Trost, B. M. J. Org. Chem (1979) 44(20) 3451–7.*

* cited by examiner

Primary Examiner—Paul J. Killos
(74) Attorney, Agent, or Firm—Todd E. Garobedian; Wiggin & Dana

(57) ABSTRACT

The present invention is directed to a process for the preparation of N-aryl amine compounds. The process of the present invention involves reacting a compound having an amino group with an arylating compound in the presence of a base and a transition metal catalyst under reaction conditions effective to form an N-aryl amine compound, the transition metal catalyst comprising a Group 8 metal and at least one chelating ligand selected from the group consisting of bisphosphines having at least one stearically hindered alkyl substituent. The formed products are valuable intermediates in the pharmaceutical and polymer fields.

21 Claims, No Drawings

TRANSITION METAL-CATALYZED PROCESS FOR PREPARING N-ARYL AMINE COMPOUNDS

DESCRIPTION OF THE RELATED ART

N-Aryl amines compounds are important substructures in natural products and industrial chemicals, such as pharmaceuticals, dyes, and agricultural products, and are useful for screening for pharmaceutical and biological activity and in the preparation of commercial polymers. It would be advantageous to prepare N-aryl amine compounds from arylating compounds such as aryl halides and/or aryl tosylates because aryl halides are generally inexpensive and readily available, while aryl tosylates are easily prepared from phenols. However, to date, methods of producing N-aryl amines are inefficient or economically unattractive. Many known processes that generate a aryl-nitrogen bond must be performed under harsh reaction conditions, or must employ activated substrates which are sometimes not available. Examples of procedures that generate aryl amine compounds include nucleophilic substitution of aryl precursors as exemplified by Hattori et al., Synthesis 1994, 199 (1994) and Bunnett, J. F., Acc. Chem. Res. 11:4132 (1978). Synthesis of arylamines via copper-mediated Uhlmann condensation reactions has also been reported (Paine, A. J., J. Am Chem. Soc. 109:1496 (1987)).

U.S. Pat. No. 5,576,460 to Buchwald et al. discloses preparation of arylamines by reacting a metal amide, such as aminostannanes or aminoboranes, with an aromatic compound having an activated substituent in the presence of a transition metal catalyst such as complexes of platinum, palladium, iron, and nickel.

In view of the above, a need exists for a general and efficient process of synthesizing N-aryl amine compounds from readily available arylating compounds. The discovery and implementation of such a method would simplify the preparation of commercially significant organic N-aryl amines and would enhance the development of novel polymers and pharmacologically active compounds. The present invention is believed to be an answer to that need.

SUMMARY OF THE INVENTION

In one aspect, the present invention is directed to a process for the preparation of N-aryl amine compounds, comprising reacting a compound having an amino group with an arylating compound in the presence of a base and a transition metal catalyst under reaction conditions effective to form an N-aryl amine compound, the transition metal catalyst comprising a Group 8 metal and at least one chelating ligand selected from the group consisting of bisphosphines having at least one stearically hindered alkyl substituent.

In another aspect, the present invention is directed to a process for the preparation of N-aryl amine compounds, comprising reacting a primary amine compound with an arylating compound selected from the group consisting of aryl chlorides and aryl tosylates, in the presence of a base and a transition metal catalyst selected from the group consisting of (R)-(–) 1-[(S)-2-(dicyclohexylphosphino) ferrocenyl]ethyldicyclohexylphosphine, (R)-(–)1-[(S)-2-(diphenylphosphino)ferrocenyl]ethyldi-t-butylphcosphine, and combinations thereof, under reaction conditions effective to form an N-arylated amine compound.

These and other aspects will become apparent upon reading the following detailed description of the invention.

DETAILED DESCRIPTION OF THE INVENTION

It now has been surprisingly found, in accordance with the present invention, that a solution is provided to the problem of providing a general and efficient process of synthesizing N-aryl amine compounds from a compound having an amino group, and an arylating compound. The present inventors have solved this problem by utilizing reaction conditions that include a base and a transition metal catalyst comprising a Group 3 metal and at least one chelating ligand selected from the group consisting of bisphosphines having at least one stearically hindered alkyl substituent. In one embodiment, the catalyst is represented by the formula:

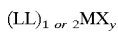

wherein (LL) is the chelating ligand, M is the Group 8 transition metal, each X is independently a monovalent anionic ligand, including, for example, a halide such as chloride or bromide; a carboxylate such as acetate; or an alkyl sulfonate such as triflate or tosylate; or X is a divalent anionic ligand, such as carbonate; and wherein y represents the total number of anionic ligands X required to balance charge, typically from 0 to about 4. In one preferred embodiment, the catalyst comprises a palladium complex of (R)-(–)1-[(S)-2-(dicyclohexylphosphino) ferrocenyl] ethyldicyclohexylphosphine and/or (F))-(–)1-[(S)-2-(diphenylphosphino)ferrocenyl]ethyldi-t-butylphosphine. The method of the present invention provides a general process for production of N-aryl amine compounds, an important class of compounds which are particularly significant in the development of pharmacologically active compounds and processing of polymers and oligomers.

The term "aryl" is defined herein as a compound whose molecules have the ring structure characteristic of benzene, naphthalene, phenanthroline, anthracene, heterocyclic, and the like. "Arylating compound" is defined as a compound which provides an aryl substituent in an organic reaction. "N-Aryl amine compounds" are those compounds in which a nitrogen atom of the compound is substituted with an aryl group. The term "bisphosphine" is herein defined as any chemical moiety having two phosphorous atoms having 3 substituents each. The phrase "stearically hindered alkyl substituent" refers to any secondary or tertiary alkyl group bonded to the phosphorous atom of the phosphine catalyst. "Ph" as defined herein is understood to represent a phenyl group.

The process of the present invention is directed to the synthesis of N-aryl amine compounds. The process of the invention comprises reacting an amine-containing compound, such as a primary amine or a secondary amine, with an arylating compound in the presence of a base and a transition metal catalyst under reaction conditions effective to form an N-aryl amine compound. The transition metal catalyst comprises a Group 8 metal and at least one chelating ligand selected from bisphosphines having at least one stearically hindered alkyl substituent.

More specifically, the process of this invention can be represented by Scheme I:

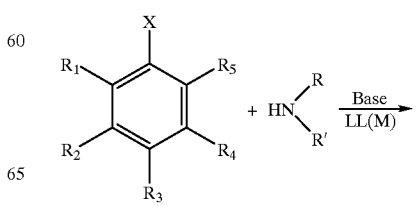

-continued

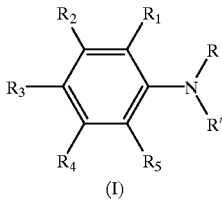

(I)

Briefly, in Scheme I, an arylating compound is reacted with an amine compound in the presence of a base, a chaelating ligand (LL), and a Group 8 metal (M) to form an N-aryl armine compound. Each of these reactions and their components are described in more detail below.

The arylating compound used in the process of the present invention may be any arylating compound of the formula (II):

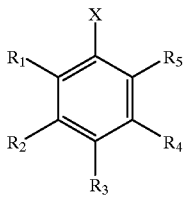

(II)

In formula II, X may be any halide atom (F, Cl, Br, I), or any sulfur-containing leaving group (e.g., triflate, sulfonate, tosylate, and the like) known in the art. Chlorides are especially preferred in the process of the present invention. $R_1$, $R_2$, $R_3$, $R_4$, and $R_5$ are independently selected from H; CN; alkyl, such as methyl, ethyl, propyl, n-butyl, t-butyl, and the like; alkoxy, vinyl, alkenyl, formyl; $CF_3$; $CCl_3$; halide, $C_6H_5$; amide such as $C(O)N(CH_3)_2$, $C(O)N(CH_2CH_3)_2$, $C(O)N(CH_2CH_2CH_3)_2$, and the like; acyl, such as $C(O)$—$C_6H_5$, and the like; ester, amino, thioalkoxy, phosphino, and the like. Arylating compound may also be a heterocyclic aromatic compound such as an azole or azole derivative, aryl phosphates, aryl trifluoroacetates, and the like. Alternatively, the arylating compound may be the process of claim 1, wherein said arylating compound any aromatic or heteroaromatic halide, such as an aromatic or heteroaromatic chloride.

Preferred arylating compounds used in the process of the invention include include aryl bromides such as chlorobenzene, 4-chloro-benzonitrile, 4-chloro-t-butyl benzene, 3-chloro-methoxy benzene, 2-chloro toluene, p-formyl pheryl chloride, p-$CF_3$ phenyl chloride, p-phenyl phenyl chloride, p-$C(O)N(CH_2CH_3)_2$ phenyl chloride, and p-$C(O)$—$C_6H_5$ phenyl chloride.

According to the method of the invention, amine-containing compounds include primary amine (e.g., R or R' is hydrogen) or secondary amine compounds (e.g., R and R' are not H). Examples of useful primary amines include aniline ($NH_2Ph$) and aminobutane ($NH_2Bu$). Examples of useful secondary amines include morphiline ($C_4H_9NO$) and piperidine ($C_5H_{11}N$)

The base shown in Scheme I is required for the process of the invention. Any base may be used so long as the process of the invention proceeds to the N-aryl amine product. It may be important in this regard that the base does not displace all of the chelating ligands on the catalyst. Nuclear magnetic resonance, infrared, and Raman spectroscopies, for example, are useful in determining whether the chelating ligands remain bonded to the Group 8 metal or whether the ligands have been displaced by the base.

Non-limiting examples of suitable bases include alkali metal hydroxides, such as sodium and potassium hydroxides; alkali metal alkoxides, such as sodium t-butoxide; metal carbonates, such as potassium carbonate, cesium carbonate, and magnesium carbonate; phosphates; alkali metal aryl oxides, such as potassium phenoxide; alkali metal amides, such as lithium amide; tertiary amines, such as triethylamine and tributylamine; (hydrocarbyl)ammonium hydroxides, such as benzyltrimethylammonium hydroxide and tetraethylammonium hydroxide; and diaza organic bases, such as 1,8-diazabicyclo[5.4.0]-undec-7-ene and 1,8-diazabicyclo-[2.2.2.]-octane. Preferably, the base is an alkali hydroxide or alkali alkoxide, more preferably, an alkali alkoxide, and most preferably, an alkali metal $C_{1-10}$ alkoxide.

The quantity of base which is used can be any quantity which allows for the formation of the N-aryl amine product. Preferably, the molar ratio of base to arylating compound ranges from about 1:1 to about 3:1, and more preferably between about 1:1 and 2:1.

The catalyst, designated (LL)M in Scheme I, is characterized as comprising a metal atom or ion (M) and at least one or more chelating ligands (LL). The metal atom or ion is required to be a Group 8 transition metal, that is, a metal selected from iron, cobalt, nickel, ruthenium, rhodium, palladium, osmium, iridium, and platinum. More preferably, the Group 8 metal is palladium, platinum, or nickel, and most preferably, palladium. The Group 8 metal may exist in any oxidation state ranging from the zero-valent state to any higher variance available to the metal.

The chelating ligand may be a neutral molecule or charged ion. A chelating ligand possesses a plurality of coordination sites, typically two, three, or four. Preferably, the chelating ligand is a bidentate ligand, that is, one having two coordination sites. The chelating ligand is also required to contain at least one element from Group 15 of the Periodic Table, preferably, at least one element of nitrogen, phosphorus, or arsenic, and more preferably phosphorus. If only one of the Group 15 elements is present, then at least a second chelating element is required, for example, oxygen or sulfur. More specifically, the chelating ligand is selected from Group 15-substituted metallocenes, such as 1,1'- or 1,2-disubstituted ferrocenes having two phosphino groups, one of which having at least one stearically hindered alkyl substituent. Addition of a stearically hindered alkyl group is advantageous in the catalyst of the present invention because the inventors have found that such substitutions allows aryl chlorides and aryl tosylates to be reacted with primary amines in highly specific and high-yielding reactions.

The term "Group 15-substituted metallocenes" as used herein includes metallocenes which are substituted with at least one Group 15-containing moiety, preferably at least one dialkyl or diaryl Group 15 moiety or hybrid thereof. Other chelating elements, for example, oxygen or sulfur, may be present. The metallocene itself comprises a transition metal atom or ion which is bonded to one or more $C_{4-8}$ multiply unsaturated hydrocarbon ring compounds. Suitable non-limiting examples of transition metal atoms in the metallocene include iron, titanium, vanadium, chromium, manganese, cobalt, nickel, molybdenum, and ruthenium. Preferably, the transition metal atom in the metallocene is iron. The $C_{4-8}$ multiply unsaturated hydrocarbon ring compounds suitably include cyclobutadiene, cyclopentadienyl, benzene, cycloheptatrienyl, and cyclooctatetraene. Representative metallocenes include ferrocene, ruthenocene, bis (benzene)chromium, bis (benzene)-molybdenum, bis (benzene)tungsten, and cobaltocenium. Non-limiting examples of ligands which classify as (helating Group 15-substituted metallocenes include 1,1'bis (diphenylphosphino)ferrocene, 1-diphenylphosphino-2-(1-dimethylamino)ethyl ferrocene, 1-diphenylarsino-1'-diphenyl-phosphino ferrocene, 1- diphenylphosphino-2-(1-diphenylphosphino)ethyl ferrocene, 1-diphenylphosphino-2-(1-di-t-butylphosphino)ethyl ferrocene, 1-diphenylphosphino-2-( 1-dicyclohexylphosphino)ethyl ferrocene, 1-dicyclohexylphosphino-2-(1-diphenylphosphino)ethyl ferrocene, 1-dicyclohexylphosphino-2-(1-dicyclohexylphosphino) ethyl ferrocene, 1-dicyclohexylphosphino-2-(1-dimethylamino)ethyl ferrocene, 1-di-t-butylphosphino-2-(1-dimethylamino)ethyl ferrocene, 1-di-i-propylphosphino-2-(1-dimethylamino)ethyl ferrocene, 1-diphenylphosphino-2-(1-dimethylamino)ethyl ferrocene, 1-[2-(diphenylphosphino)ferrocenyl]ethyl methyl ether, 1-[2-(dicyclohexylphosphino)ferrocenyl]ethyl methyl ether, 1-[2-(di-i-propylphosphino)ferrocenyl]ethyl methyl ether, 1-[2-(di-t-butylphosphino)ferrocenyl]ethyl methyl ether, (−)-(R)-N,N-dimethyl-1-[(S)-1',2-bis(diphenylphosphino)ferrocenyl]ethylamine, (+)-(S)-1-[(R)-2-(diphenylphosphino)ferrocenyl]ethyl methyl ether, and N,N-dimethyl-1,2-bis(di-t-butylphosphino) ferrocenyl] ethylamine. Analogous phosphine and amine substituted derivatives of the aforementioned metallocenes may also be employed. Preferably, the Group 15-substituted metallocene is a Group 15-substituted ferrocene, more preferably, a phosphoferrocene, and most preferably (R)-(−)1-[(S)-2-(dicyclohexylphosphino)ferrocenyl]ethyldicyclohexylphosphine or (R)-(−)1-[(S)-2-(diphenylphosphino)ferrocenyl]ethyldi-t-butylphosphine.

Many of the aforementioned metal catalysts which are beneficially employed in the process of this invention can be represented by the following formula:

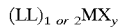

$(LL)_{1\ or\ 2}MX_y$ wherein (LL) is the chelating ligand, M is the Group 8 transition metal, each X is independently a monovalent anionic ligand, including for example a halide, such as chloride or bromide; a carboxylate, such as acetate; or an alkyl sulfonate, such as triflate; or X is a divalent anionic ligand, such as sulfonate or carbonate; and wherein y represents the total number of anionic ligands X required to balance charge, typically from 0 to about 4. Alternatively, X can be a neutral dative ligand such as dibenzylidene acetone, cyclooctadiene, ethylene, triphenylphosphine, or other neutral ligand. It is to be understood that any of the chelating ligands described earlier may be used in the above formula. Non-limiting examples of suitable transition metal complexes include dichloro-[1,1'-bis(diphenylphosphino) ferrocene]palladium (II), dichloro-[1,1'-bis (diphenylphosphino)-2,2'-binapthyl]palladium (II), dichloro-[1,2-bis(diphenylarsino)benzene]platinum (II), 1,2-bis[(diphenylphosphino)benzene]platinum (II) acetate, dichloro-[1-diphenylphosphino-2-(1-dimethylamino) ethylferrocene]palladium (II), and analogous complexes containing bidentate ligands mentioned hereinbefore with iron, cobalt, nickel, ruthenium, rhodium, osmium, and iridium as the metal component.

Methods for preparing the aforementioned catalysts are known to those skilled in the art. For a description of general synthetic techniques, see *Inorganic Synthesis: Reagents for Transition Metal Complex and Organometallic Systems*; R. J. Angelici, Ed., Wiley-Interscience: New York, 1990, Vol. 28, pp. 77–135 (Chapter 2), incorporated herein by reference, wherein representative preparations of Group 8 complexes containing chelating amine, phosphine, and arsine ligands are taught.

As an alternative embodiment of this invention, the catalyst may be anchored or supported on a catalyst support, including a refractory oxide, such as silica, alumina, titania, or magnesia; or an aluminosilicate clay, or molecular sieve or zeolite; or an organic polymeric resin.

Heretofore, the transition metal catalyst has been described as comprising a transition metal and a chelating ligand. It is not precisely known, however, whether both, one, or neither donor atoms of the chelating ligand are bound to the transition metal during the entire process of this invention or whether the chelating ligand is in a labile or non-bonded configuration relative to the transition metal during part or all of the process. Generally, it is believed that the chelating ligand is bonded through the Group 15 element to the transition metal; however, such a theory should not be binding upon the invention in any manner. Modern analytical techniques, such as nuclear magnetic resonance spectroscopy ($^{13}C$, $^1H$, $^{31}P$), infrared and Raman spectroscopies, and X-ray diffraction, may assist in the determination of initial catalyst structure and changes in structure throughout the process.

The transition metal catalyst may be synthesized first and thereafter employed in the arylation process. Alternatively, the catalyst can be prepared in situ in the arylation reaction mixture. If the latter mixture is employed, then a Group 8 catalyst precursor compound and the desired chelating ligand are independently added to the reaction mixture wherein formation of the transition metal catalyst occurs in situ. Suitable precursor compounds include alkene and diene complexes of the Group 8 metals, preferably, di(benzylidene)acetone (dba) complexes of the Group 8 metals, as well as, monodentate phosphine complexes of the Group 8 metals, and Group 8 carboxylates. In the presence of the chelating ligand, in situ formation of the transition metal catalyst occurs. Non-limiting examples of suitable precursor compounds include [bis-di(benzylidene)acetone] palladium (0), tetrakis-(triphenylphosphine)-palladium (0), tris-[di(benzylidene)acetone]palladium (0), tris-[di (benzylidene) acetone]-dipalladium (0), palladium acetate, and the analogous complexes of iron, cobalt, nickel, ruthenium, rhodium, osmium, iridium, and platinum. Any of the aforementioned catalyst precursors may include a solvent of crystallization. Group 8 metals supported on carbon, preferably, palladium on carbon, can also be suitably employed as a precursor compound. Preferably, the catalyst precursor compound is bis-[di(benzylidene)acetone] palladium(0).

The quantity of transition metal catalyst which is employed in the process of this invention is any quantity which promotes the formation of the N-aryl product. Generally, the quantity is a catalytic amount, which means that the catalyst is used in an amount which is less than stoichiometric relative to the unsaturated organic sulfonate. Typically, the transition metal catalyst ranges from about 0.01 to about 20 mole percent, based on the number of moles of the compound having at least one unsaturated nitrogen atom used in the reaction. Preferably, the quantity of transition metal catalyst ranges from about 1 to about 10 mole percent, and more preferably from about 3 to about 8 mole percent, based on the moles of the unsaturated nitrogen-containing compound.

The process described herein may be conducted in any conventional reactor designed for catalytic processes.

Continuous, semi-continuous, and batch reactors can be employed. If the catalyst is substantially dissolved in the reaction mixture as in homogeneous processes, then batch reactors, including stirred tank and pressurized autoclaves, can be employed. If the catalyst is anchored to a support and is substantially in a heterogeneous phase, then fixed-bed and fluidized bed reactors can be used. In the typical practice of this invention the compound having an amino group, arylating compound, base, and catalyst are mixed in batch, optionally with a solvent, and the resulting mixture is maintained at a temperature and pressure effective to prepare the N-arylated product.

Any solvent can be used in the process of the invention provided that it does not interfere with the formation of the N-aryl amine product. Both aprotic and protic solvents and combinations thereof are acceptable. Suitable aprotic solvents include, but are not limited to, aromatic hydrocarbons, such as toluene and xylene, chlorinated aromatic hydrocarbons, such as dichlorobenzene, and ethers, such as tetrahydroturan. Suitable protic solvents include, but are not limited to, water and aliphatic alcohols, such as ethanol, isopropanol, and cyclohexonol, as well as glycols and other polyols. The amount of solvent which is employed may be any amount, preferably an amount sufficient to solubilize, at least in part, the reactants and base. A suitable quantity of solvent typically ranges from about 1 to about 100 grams solvent per gram reactants. Other quantities of solvent may also be suitable, as determined by the specific process conditions and by the skilled artisan.

Generally, the reagents may be mixed togethe(r or added to a solvent in any order. Air is preferably removed from the reaction vessel during the course of the reaction, however this step is not always necessary. If it is desirable or necessary to remove air, the solvent and reaction mixture can be sparged with a non-reactive gas, such as nitrogen, helium, or argon, or the reaction may be conducted under anaerobic conditions. The process conditions can be any operable conditions which yield the desired N-aryl product. Beneficially, the reaction conditions for this process are mild. For example, a preferred temperature for the process of the present invention ranges from about ambient, taken as about 22° C., to about 150° C., and preferably, from about 80° C. to about 110° C. The process may be run at subatmospheric pressures if necessary, but typically proceeds sufficiently well at about atmospheric pressure. The process is generally run for a time sufficient to convert as much of the unsaturated nitrogen-containing compound to product as possible. Typical reaction times range from about 30 minutes to about 24 hours, but longer times may be used if necessary.

The N-arylated amine product can be recovered by conventional methods known to those skilled in the art, including, for example, distillation, crystallization, sublimation, and gel chromatography. The yield of product will vary depending upon the specific catalyst, reagents, and process conditions used. For the purposes of this invention, "yield" is defined as the mole percentage of N-aryl amine product recovered, based on the number of moles of unsaturated nitrogen-containing compound employed. Typically, the yield of N-aryl amine product is greater than about 25 mole percent. Preferably, the yield of N-aryl amine product is greater than about 60 mole percent, and more preferably, greater than about 80 mole percent.

The following examples are intended to illustrate, but in no way limit the scope of the present invention. All parts and percentages are by weight and all temperatures are in degrees Celsius unless explicitly stated otherwise.

General Methods: $^1$H and $^{13}$C{$^1$H} NMR spectra were recorded on a QE 300 MHz spectrometer with TMS ($^1$H) or residual protiated ($^{13}$C) solvent used as a reference. $^{31}$P{$^1$H} NMR spectra were recorded on an Omega 300 MHz spectrometer with shifts reported relative to an external 85% $H_3PO_4$ standard; resonances downfield of the standard are reported as positive. Toluene solvent was distilled from sodium and benzophenone. Dioxane solvent was purchased anhydrous from Aldrich. Tech grade hexanes was distilled before use in chromatography. All other solvents were used as received.

The compounds and catalysts used in the following examples were synthesized by the following procedures. In these procedures, Ligand 1 is 1,1-bis-(di-t-butylphosphino) ferrocene (DB$^t$PF), Ligand 2 is (R)-(–)1-[(S)-2-(dicyclohexylphosphino) ferrocenyl] ethyldicyclohexylphosphine, and Ligand 3 is (R)-(–)1-[(S)-2-(diphenylphosphino)ferrocenyl]ethyldi-t-butylphosphine.

1,1'-Bis(di-tert-butylphosphino)ferrocene (Ligand 1, DB$^t$PF) was prepared by literature procedures (Cullen, W. R.; Kim, T. J.; Einstein, F. W. B.; Jones, T. Organometallics 1983, 2, 714–19). $^1$H NMR: ($C_6D_6$) δ 4.25 (m, 4H), 4.20 (m, 4H), 1.24 (s, 18H), 1.21 (s, 18H); $^{13}$C{$^1$H} NMR: ($C_6D_6$) δ 79.75 (d, J=31.7 Hz), 74.23 (d, J=11.7 Hz), 71.65 (d, J=2.0 Hz), 32.81 (d, J=22.4 Hz), 31.00, 25.69; $^{31}$P{$^1$H} NMR: ($C_6D_6$) δ 27.08.

General Procedure A: 4-Chlorotoluene (126 mg, 1.00 mmol), Pd(DBA)$_2$ (17.3 mg, 0.0300 mmol or 11.5 mg, 0.0230 mmol), DB$^t$PF (21.3 mg, 0.0450) or ligand 2 (16.2 mg, 0.030 mmol) or ligand 3 (18.2 mg, 0.030 mmol) and NaO$^t$Bu (115 mg, 1.20 mmol) were suspended in 1 mL of toluene or dioxane in a screw-capped vial. The vial was sealed with a cap containing a PTFE septum and removed from the dry box. Aniline (100 μL, 1.10 mmol) was added to the reaction mixture by syringe. The vial was heated in a 110° C. oil bath. Over this time, a large amount of solid (presumably NaCl) formed. Reactions were cooled to room temperature and worked-up according to the procedures described below.

General Procedure B: The chloroarene (126 mg, 1.00 mmol), Pd(OAc)$_2$ (2.2 mg, 0.010 mmol), DB$^t$PF (7.1 mg, 0.015 mmol) or Ligand 2 (8.1 mg, 0.015 mmol) or Ligand 3 (9.1 mg, 0.015 mmol) and NaO$^t$Bu (115 mg, 1.20 mmol) were suspended in 1 mL of toluene in a screw-capped vial. The vial was sealed with a cap containing a PTFE septum and removed from the dry box. Aniline (109 μL, 1.20 mmol) n-butylamine (119 μL, 1.20 mmol) or piperidine (119 μL, 1.20 mmol) was added to the reaction mixture by syringe. The vial was heated in an oil bath at the temperature and time stated in Table 1. Over this time, a large amount of solid (presumably NaCl) formed. Reactions were cooled to room temperature, and worked-up according to the procedures described below.

N-4-tolylaniline This compound was prepared from several methods (Driver, M. S.; Hartwig, J. F. *J. Am. Chem. Soc.* 1996, 118, 7217–7218).

A. From ArCl using Pd(dba)$_2$ as catalyst precursor: Procedure A was followed. After the reaction was judged complete by GC analysis, the reactions were concentrated in vacuo. The crude products were purified by sublimation at 120° C. and 0.25 Torr. $^1$H NMR: (CDCl$_3$) δ 7.27 (dd, J=7.3, 8.7 Hz, 2H,), 7.12 (d, J=8.3 Hz, 2H,), 7.01–7.08 (m, 4H), 6.91 (t, J=7.3 Hz, 1H), 5.63 (s, 1H), 2.34 (s, 3H); $^{13}$C{$^1$H} NMR: (CDCl$_3$) δ 144.10, 140.44, 131.10, 130.04, 129.79, 120.47, 119.08, 117.03, 20.89.

B. From ArCl using Pd(OAc)$_2$ as catalyst precursor: Procedure B was followed. After the reaction was judged complete by GC analysis, the reactions were diluted with THF and adsorbed onto silica gel. Silica gel chromatography eluting 1to with 20:1 hexanes:ethyl acetate gave a white solid (176 mg, 96%).

C. From ArBr: 4-Bromotoluene (174 mg, 1.02 mmol), Pd(DBA)$_2$ (29.3 mg, 0.051 mmol),DB$^t$PF (36.3 mg, 0.076 mmol) and NaO$^t$Bu (118 mg, 1.23 mmol) were suspended in 1 mL of toluene in a screw-capped vial. The vial was sealed with a cap containing a PTFE septum and removed from the dry box. Aniline (102 µL, 1.12 mmol) was added to the reaction mixture by syringe. The vial was stirred at room temperature for 20 hours. Over this time, a large amount of solid (presumably NaBr) formed. The reaction was concentrated in vacuo. The crude product was purified by sublimation at 120° C. and 0.25 torr.

N-Butyl-2-methylaniline This compound was prepared by several different procedures (Louie, J.; Driver, M. S.; Hamann, B. C.; Hartwig, J. F. *J. Org. Chem.* 1997, 62, 1268–1273).

A. Using DB$^t$BF and Pd(dba)$_2$ as catalyst precursor: Procedure A was followed using 2-chlorotoluene (133 mg, 1.05 mmol) and butylamine (116 µL, 1.15 mmol). The crude reaction was diluted with toluene (50 mL) and was washed with water (50 mL, 1×) followed by brine (50 mL, 1×). The organic layer was dried over Na$_2$SO$_4$, filtered, and concentrated in vacuo. The product was isolated in 67% yield after silica gel chromatography using 5% EtOAc in hexanes. $^1$H NMR: (CDCl$_3$) δ 7.14 (dd, J=8.0, 7.5 Hz, 1H), 7.02 (d, J=7.6 Hz, 1H), 6.60–6.70 (m, 2H), 3.44 (bs, 1H), 3.18 (t, J=7.1 Hz, 2H), 2.15 (s, 3H), 1.68 (m, 2H), 1.48 (m, 2H), 1.00 (t, J=7.4 Hz, 3H); $^{13}$C{$^1$H} NMR: (CDCl$_3$) δ 146.36, 129.94, 127.08, 121.60, 116.55, 109.54, 43.59, 31.69, 20.34, 17.40, 13.90.

B. Using ligands 2 and 3 with Pd(OAc)$_2$ as catalyst precursor: Procedure B was followed. The crude reaction was diluted with THF and adsorbed onto silica gel. Silica gel chromatography using 20:1 hexanes:ethyl acetate as eluent gave a clear oil. Using Ligand 2, 153 mg (94% yield) of product was obtained. Using Ligand 3, 156 mg (96% yield) of product was obtained.

N-Butyl-4-methylaniline (Watanabe, Y.; Tsuji, Y.; Ige, H.; Ohsugi, Y.; Ohta, T. *J. Org. Chem.* 1984, 49, 3359–3363). Procedure B was also followed using ligands 2 and 3. The crude reactions were diluted with THF and adsorbed onto silica gel. Silica gel chromatography using 20:1 hexanes:ethyl acetate as eluent gave a clear oil. Using Ligand 2, 153 mg (94% yield) of product was obtained. Using Ligand 3, 150 mg (92% yield) of product was obtained. $^1$H NMR (C$_6$D$_6$): δ 7.02 (d, J=8.3 Hz, 2H), 6.45 (d, J=8.3 Hz, 2H), 2.95 (br s, 1H), 2.81 (q, J=6.5 Hz, 2H), 2.21 (s, 3H), 1.23 (m, 2H), 1.17 (m, 2H), 0.78 (t, J=7.0 Hz, 3H); $^{13}$C{$^1$H} NMR: (C$_6$D$_6$) δ 146.87, 129.98, 125.94, 113.17, 43.97, 31.89, 20.60, 20.49, 14.05.

N-Hexyl-4-methylaniline (Wolfe, J. P.; Buchwald, S. L. *J. Org. Chem.* 1997, 62, 6066–6068). 4-methylphenyl-p-toluene sulfonate (262 mg, 1.00 mmol), Pd(OAc)$_2$ (4.4 mg, 0.020 mmol) Ligand 2 (16.3 mg, 0.030 mmol), and sodium t-buloxide (117 mg, 1.22 mmol) were suspended in 3 mL of toluene in a screw-capped vial. The vial was sealed with a cap containing a PTFE septum and removed from the dry box. n-Hexylamine (158 µL, 1.20 mmol) was added by syringe. The reaction was heated for 2 h at 110° C., after which time the aryl tosylate had been consumed as determined by GC. Over this time, a large amount of solid (presumably NaOTs) formed. The reaction was diluted with ethyl acetate and adsorbed onto silica gel. Silica gel chromatography eluting with 20:1 hexanes:ethyl acetate gave 157 mg (82% yield) of a pale yellow oil. $^1$H NMR (CDCl$_3$): δ 7.00 (d, J=8.0 Hz, 2H), 6.56 (d, J=8.0 Hz, 2H), 3.47 (br s, 1H), 3.10 (t, J=7.0 Hz, 2H), 2.26 (s, 3H), 1.62 (m, 2H), 1.25 (m, 6H), 0.92 (m, 3H); $^{13}$C{$^1$H} NMR: (CDCl$_3$) δ 146.27, 129.65, 126.20, 112.85, 44.35, 31.65, 29.56, 26.85, 22.61, 20.33, 14.03.

4-(3-Anisole)morpholine (Kawaguchi, M.; Ohashi, O. *Synthesis* 1985, 701–703) 3-Chloroanisole (152 mg, 1.06 mmol) Pd(OAc)$_2$ (2.2 mg, 0.010 mmol), DB$^t$PF (7.1 mg, 0.015 mmol) and NaO$^t$Bu (115 mg, 1.20 mmol) were suspended in 1 mL of toluene in a screw-capped vial. The vial was sealed with a cap containing a PTFE septum and removed from the dry box. Morpholine (102 µL, 1.17 mmol) was added to the reaction mixture by syringe. The vial was heated in an oil bath for 10 h at 100° C., after which time the aryl chloride had been consumed as judged by GC. Over this time, a large amount of solid (presumably NaCl) formed. The reaction was diluted with THF and adsorbed Dnto silica gel. Silica gel chromatography eluting with 5:1 hexanes:ethyl acetate gave 156 mg (81% yield) of product. $^1$H NMR: (CDCl$_3$) δ 7.16 (dd, J=7.7, 7.7 Hz, 1H), 6.50 (dd, J=2.2, 1.3 Hz, 1H), 6.44–6.40 (m, 2H), 3.81 (t, J=4.9 Hz, 4H), 3.76 (s, 3H), 3.10 (t, J=4.9 Hz, 4H); $^{13}$C{$^1$H} NMR: (CDCl$_3$) δ 160.43, 152.51, 129.6, 108.22, 04.44, 101.95, 66.67, 54.95, 49.04.

1-(4-methylphenyl)piperidine (Louie, J.; Driver, M. S.; Hamann, B. C.; Hartwig, J. F. *J. Org. Chem.* 1997, 62, 1268–1273). Procedure B was followed using DB$^t$PF as ligand. The crude reaction was diluted with THF and adsorbed onto silica gel. Silica gel chromatography using 20:1 hexanes:ethyl acetate as eluent gave a clear oil. Using DB$^t$PF, 158 mg (90% yield) of product was obtained. $^1$H NMR (C$_6$D$_6$): δ 1.30 (m, 2H), 1.48 (m, 4H), 2.19 (s, 3H), 2.90 (t, J=5.5 Hz, 4H), 6.82 (d, J=8.4 Hz, 2H), 7.03 (d, J=8.4 Hz, 2H); $^{13}$C{$^1$H} NMR (C$_6$D$_6$): δ 20.59, 24.47, 26.27, 51.33, 117.38, 128.44, 129.78, 150.94.

4-Cyanodiphenylamine (Takeuchi, H.; Takano, K. *J. Chem. Soc. Perkin Trans.* 1 1986, 611–618. 4-Cyanophenyltosylate (271 mg, 1.02 mmol), Pd(DBA)$_2$ (11.7 mg, 0.02 mmol), DB$^t$PF (14.5 mg, 0.03 mmol) and sodium 2,4,6-tri-t-butylphenoxide (346 mg, 1.22 mmol) were suspended in 2 mL of toluene in a screw-capped vial. The vial was sealed with a cap containing a PTFE septum and removed from the dry box. Aniline (102 µL, 1.12 mmol) was added to the reaction mixture by syringe. The vial was heated in a 110° C. oil bath for 16 hours. Over this time, a large amount of solid (presumably NaOTs) formed. The reaction was cooled to room temperature. The crude reaction was diluted with toluene (50 mL) and washed with water (50 mL, 1×) followed by brine (50 mL, 1×). The organic layer was dried over Na$_2$SO$_4$, filtered, and concentrated in vacuo. Purified product was obtained in 82% yield after silica gel chromatography using 10% EtOAc in hexanes. $^1$H NMR: (CDCl$_3$) δ 7.41 (d, J=8.7 Hz, 214), 7.33 (m, 2H) 6.08 (m, 3H), 6.96 (d, J=8.7 Hz, 2H), 6.43 (bs, 1H); $^{13}$C{$^1$H} NMR: (CDCl$_3$) δ 148.01, 139.64, 133.50, 129.38, 123.56, 120.87, 120.01, 114.64, 100.63.

N-Butyl-4-butylaniline (Hamann, B. C.; Hartwig, J. F. *J. Am. Chem. Soc.* 1998, 120, 3694–3703). 4-iodobutylbenzene (272 mg, 1.04 mmol), Pd(DBA)$_2$ (5.8 mg, 0.01 mmol), DB$^t$PF (7.1 mg, 0.015 mmol) and NaO$^t$Bu (115 mg, 1.20 mmol) were suspended in 1 mL of toluene in a screw-capped vial. The vial was sealed with a cap containing a PTFE septum and removed from the dry box. n-Butylamine (119 µL, 1.20 mmol) was added to the reaction mixture by syringe. The reaction was stirred at room temperature for 24 hours. Over this time, a large amount of solid (presumably NaI) formed. The crude reaction was diluted with toluene (50 mL) and washed with water (50 mL, 1×) followed by brine (50 mL, 1×). The organic layer was dried over Na$_2$SO$_4$, filtered, and concentrated in vacuo. Purified product was obtained in 51% yield after silica gel chromatography using 5% EtOAc in hexanes. $^1$H NMR: (CDCl$_3$) δ 7.03 (d, J=8.4 Hz, 2H), 6.59 (d, J=8.4 Hz, 2H) 3.45 (bs, 1H), 3.12 (t, J=7.1 Hz, 2H), 2.54 (t, J=7.6 Hz, 2H) 1.66–1.50 (m, 4H), 1.47–1.34 (m, 4H), 0.99 (t, J=7.3 Hz, 3H), 0.95 (t, J=7.3 Hz, 3H); $^{13}$C{$^1$H} NMR: (CDCl$_3$) δ 146.28, 131.62, 129.03, 112.81, 44.05, 34.68, 34.01, 31.67, 22.30, 20.28, 13.96, 13.89.

N-Butyl-2,4-dimethylaniline (Reilly, J.; O'Neill, B. *J. Chem. Soc. Ind. London* 1927, 46, 226T–227T). 4-Iodo-meta-xylene (232 mg, 1.00 mmol), Pd(DBA)$_2$ (5.8 mg, 0.01 mmol), DB$^t$PF (7.1 mg, 0.015 mmol) and NaO$^t$Bu (115 mg, 1.20 mmol) were suspended in 1 mL of toluene in a screw-capped vial. Butylamine (111 μL, 1.10 mmol) was added by syringe. The reaction was stirred at room temperature for 7 hours. Over this time, a large amount of solid (presumably NaI) formed. The crude reaction was diluted with toluene (50 mL) and washed with water (50 mL, 1×) followed by brine (50 mL, 1×). The organic layer was dried over Na$_2$SO$_4$, filtered, and concentrated in vacuo. Purified product was obtained in 52% yield after silica gel chromatography using a gradient of hexanes to 2% EtOAc in hexanes. $^1$H NMR: (CDCl$_3$) 6.91 (d, J=7.9 Hz, 1H), 6.86 (s, 1H), 6.51 (d, J=7.9 Hz, 1H), 3.26 (bs, 1H), 3.13 (t, J=7.1 Hz, 2H), 2.22 (s, 3H), 2.09 (s, 3H), 1.62 (m, 2H), 1.44 (m, 2H), 0.95 (t, J=7.3 Hz, 3H) $^{13}$C{$^1$H} NMR: (CDCl$_3$) δ 144.12, 130.82, 127.30, 125.65, 121.77, 109.79, 43.89, 31.72, 20.37, 20.28, 17.36, 13.93.

4-Butyldiphenylamine (Takada, A.; Nishimura, H. *Chem. Pharm. Bull.* 1962, 10, 1–8) Butyl iodobenzene (261 mg, 1.00 mmol), Pd(DBA)$_2$ (5.8 mg, 0.01 mmol), DB$^t$PF (7.1 mg, 0.015 mmol) and NaO$^t$Bu (115 mg, 1.20 mmol) were suspended in 2 mL of toluene in a screw-capped vial. The vial was sealed with a cap containing a PTFE septum and removed from the dry box. Aniline (100 μL, 1.10 mmol) was added to the reaction mixture by syringe. The vial was stirred at room temperature for 24 h. Over this time, a large amount of solid (presumably NaI) formed. The crude reaction was diluted with toluene (50 mL) and washed with water (50 mL, 1×) followed by brine (50 mL, 1×). The organic layer was dried over Na$_2$SO$_4$, filtered, and concentrated in vacuo. Purified product was obtained in 94% yield after filtration through silica gel using 5% EtOAc in hexanes as the eluent. $^1$H NMR: (CDCl$_3$) δ 7.21 (t, J=8.0 Hz, 2H), 7.06 (d, J=8.4 Hz, 2H), 6.99–6.96 (m, 4H), 6.85 (t, J=7.3 Hz, 1H), 5.54 (bs, 1H), 2.54 (t, J=7.5 Hz, 2H), 1.57 (m, 2H), 1.35 (m, 2H), 0.92 (t, J=7.3 Hz, 3H); $^{13}$C{$^1$H} NMR: (CDCl$_3$) δ 143.79, 140.39, 135.92, 129.21, 129.13, 120.21, 118.61, 116.86, 34.89, 33.79, 22.31, 13.92.

EXAMPLES 1–19

The known ligand DB$^t$PF (1,1'-bis-(di-t-butylphosphino) ferrocene, Ligand 1) was evaluated in the amination reactions. DB$^t$PF is air sensitive over long periods of time in solution, but can be handled and weighed in air. Table 1 summarizes the results with this ligand and others discussed below in the general reaction presented in Scheme I. In Table 1, yields are for pure isolated product and are an average of 2 runs on a 1 mmol scale using 0.5–1.0M concentrations, except for entry 15 (0.1 mmol scale).

TABLE 1

Hindered, chelating alkylphosphines in the amination of aryl halides and tosylates.

| | Amine | ArX | Product | Catalyst | Conditions | Yield |
|---|---|---|---|---|---|---|
| 1 | NH$_2$Ph | —⟨⟩—Cl | —⟨⟩—NH—Ph | 3 mol % Pd(dba), Ligand 1 | 110° C., 24 h | 93% |
| 2 | NH$_2$Ph | —⟨⟩—Cl | —⟨⟩—NH—Ph | 3 mol % Pd(dba), Ligand 1 | 110° C. 4 h | 93% |
| 3 | NH$_2$Ph | —⟨⟩—Cl | —⟨⟩—NH—Ph | 2 mol % Pd(dba), Ligand 2 | 110° C. 16 h | 99% |
| 4 | NH$_2$Ph | —⟨⟩—Cl | —⟨⟩—NH—Ph | 1 mol % Pd(OAc), Ligand 2 | 85° C. 12 h | 92% |
| 5 | NH$_2$Ph | —⟨⟩—Cl | —⟨⟩—NH—Ph | 2 mol % Pd(dba), Ligand 3 | 110° C. 16 h | 96% |
| 6 | NH$_2$Ph | —⟨⟩—Cl | —⟨⟩—NH—Ph | 1 mol % Pd(dba), Ligand 1 | 110° C. 24 h | 57% |

TABLE 1-continued

Hindered, chelating alkylphosphines in the amination of aryl halides and tosylates.

| | Amine | ArX | Product | Catalyst | Conditions | Yield |
|---|---|---|---|---|---|---|
| 7 | NH$_2$Bu | 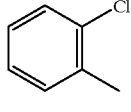 | 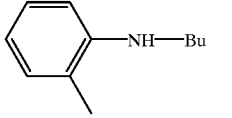 | 1 mol % Pd(OAc), Ligand 2 | 85° C. 2 h | 89% |
| 8 | NH$_2$Bu | 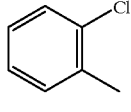 | 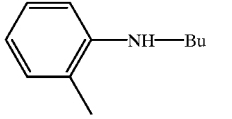 | 1 mol % pd(OAc), Ligand 3 | 85° C. 2 h | 94% |
| 9 | NH$_2$Bu | 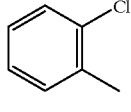 | 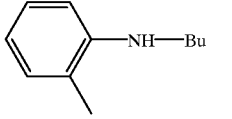 | 1 mol % Pd(Oac), Ligand 2 | 85° C. 2 h | 89% |
| 10 | NH$_2$Bu |  | 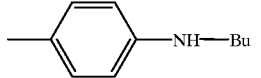 | 1 Mol % Pd(OAc), Ligand 3 | 85° C. 12 h | 87% |
| 11 |  | 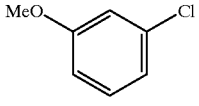 | 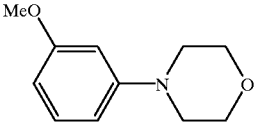 | 1 mol % Pd(OAc), Ligand 1 | 100° C. 10 h | 81% |
| 12 |  |  | 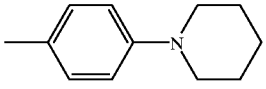 | 1 mol % Pd(OAc), Ligand 1 | 100° C. 12 h | 85% |
| 13 | NH$_2$Ph | 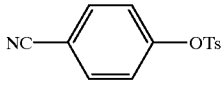 | 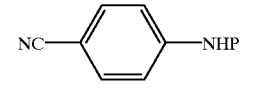 | 2 mol % Pd(dba)$_2$, Ligand 1 | 110° C. 16 h | 79% |
| 14 | NH$_2$Bu | 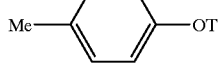 | 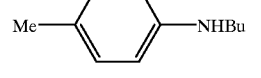 | 5 mol % Pd(OAc)$_2$ Ligand 2 | 110° C. 2 h | 67% |
| 15 | NH$_2$Bu | 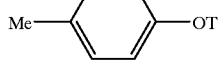 | 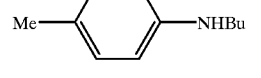 | 3 mol % Pd(OAc)$_2$ Ligand 2 | 110° C. 18 h | 60% |
| 16 | NH$_2$Bu | 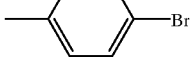 | 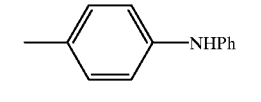 | 5 mol % Pd(dba)$_2$ Ligand 1 | r.t., 20 h | 94% |
| 17 | NH$_2$Bu | 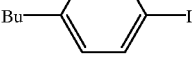 | 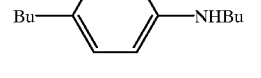 | 1 mol % Pd(dba)$_2$ Ligand 1 | r.t., 24 h | 47% |
| 18 | NH$_2$Bu | 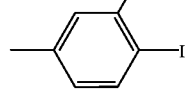 | 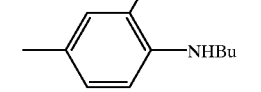 | 1 mol % Pd(dba)$_2$ Ligand 1 | r.t., 7 h | 49% |

TABLE 1-continued

Hindered, chelating alkylphosphines in the amination of aryl halides and tosylates.

| | Amine | ArX | Product | Catalyst | Conditions | Yield |
|---|---|---|---|---|---|---|
| 19 | NH$_2$Ph | Bu—〈aryl〉—I | Bu—〈aryl〉—NHPh | 1 mol % Pd(dba)$_2$ Ligand 1 | r.t., 24 h | 95% |

The results of the amination reactions illustrate (1) remarkable rate enhancements for reactions with sterically hindered alkylphosphine ligands, (2) mild conditions for aminations of aryl chlorides, (3) amination of aryl tosylates, and (4) preparation of mixed alky arylamines in high yields by the metal-catalyzed amination of unactivated aryl chlorides with primary alkylamines.

DB$^t$PF leads to exceptionally high-yield amination of activated aryl chlorides with aniline (Table 1, entry 1). Reactions were complete after 1 d at 110° C. in toluene solvent, but were complete in only 4 h in dioxane solvent (entry 2). Entry 6 shows that this ligand allows for the palladium-catalyzed amination of aryl chlorides with primary alkylamines in acceptable yields. Diarylation and competing hydrodehalogenation are assumed to be competing reactions in this case. Entries 11 and 12 show that this ligand provides excellent yields of dialkyl anilines from unactivated aryl chlorides under much milder conditions that previous palladium-catalyzed chemistry with unactivated chloroarenes. Previous unpublished work in our laboratory showed that palladium complexes of 1,1'-bis-(dimethylphosphino)ferrocene were ineffective catalysts for the amination chemistry. This result, in combination with those reported here, shows the importance of ligand steric hindrance.

Other chelating ligands with large bite angles created by backbones that are stable to basic conditions, while containing bulky alkyl substituents at the phosphorus, include Ligand 2 used by Lonza for the stereoselective reduction of biotin (Imwinkelreid, R. Chimia 51:300–302, 1997), reported by Togni et al. for asymmetric hydrogenation (Togni, A. et al., Inorg. Chim. Acta 222:213–214, 1994; Zanetti, N. C. et al., Organometallics 15:860–866, 1996). These ligands induced aminations of unactivated aryl chlorides with primary amines under remarkably mild conditions. Ligands 2 and 3 were evaluated for the amination of hindered and unhindered aryl chlorides with aniline and butylamine. High yields of aryl chloride amination were observed with aniline (entries 3–5). The reaction in entry 4 that employs palladium acetate as catalyst precursor, occurs under conditions reminiscent of previous aminations of aryl bromides. Table 2 shows that no diarylation of aniline was observed when using Ligand 2.

TABLE 2

Effect of ligand on monoarylation vs. diarylation selectivity for 4-chlorotoluene and n-butylamine

| Ligand | Amine (H$_2$NR) | HNArR:NAr$_2$R |
|---|---|---|
| 1 | R = Bu | 3.3:1 |
| 2 | R = Bu | 130:1 |
| 3 | R = Bu | 30:1 |
| 2 | R = Ph | diarylation product not detected |

In addition, high yields of mixed alkyl aryl amines were obtained by employing these two ligands. Isolated yields between 87% and 94% were obtained when using Ligands 2 or 3 with palladium acetate at only 85° C. for 2–12 h for either hindered or unhindered aryl chlorides. Palladium precursors and Ligands 2 and 3 catalyzed the amination of secondary amines only slowly, perhaps due to the exquisite selectivity for monoarylation, as shown in Table 2. More rapid arylation of secondary amines was obseeved with Ligand 1 in combination of Pd(OAc)$_2$ providing an excellent catalyst for the arylation of secondary amines as above.

Previous studies on the palladium-catalyzed amination of aryl chlorides catalyzed by monodentate alkylphosphines required activated aryl chlorides and were limited to secondary amines (Reddy, N. P. et al., Tetrahedron Lett. 38:4807–4810, 1997; Beller, M. et al., Tetrahedron Lett. 38:2073–2074, 1997). Activation of chloroarenes by nickel is well established and nickel-catalyzed amination of aryl chlorides had been reported (Wolfe, J. P. et al., J. Am. Chem. Soc. 119:6054–6058, 1997). The work here shows that palladium-catalyzed chemistry, which is often less air sensitive and more general, can lead to amination of unactivated aryl chlorides in toluene solvent and with primary alkylamines.

Entries 13–15 show that hindered, chelating alkylphosphine ligands also generate effective catalysts for the amination of aryl tosylates. The reaction yields with unactivated aryl tosylates are remarkable, considering that little palladium-catalyzed cross-coupling with any type of aryl arene sulfonate has been reported. These results illustrate the potential of using the chelating alkyl phosphine catalysts of the invention in chemistries that convert phenols to amines using tosyl chloride instead of triflic anhydride to activate the phenol.

Ligand 1 allowed for aminations of aryl bromides with aniline in excellent yield at room temperature (entry 16). Previous room temperature palladium-catalyzed amination chemistry required aryl iodides and the addition of crown ethers (Wolfe et al., J. Org. Chem. 62:6066–6068, 1997), and aminations with aniline substrates required heating. Entries 17–19 show the room temperature amination of aryl iodides without additives. In all cases, complete consumption of the aryl iodide occurred before 24 h had elapsed. Yields for the amination of aryl iodides with primary alkylamiries were acceptable. However, the yields for amination of the unactivated aryl iodide in entry 19 with primary arylamines were excellent.

Although the invention has been shown and described with respect to illustrative embodiments thereof, it should be appreciated that the foregoing and various other changes, omissions and additions in the form and detail thereof may be made without departing from the spirit and scope of the invention as delineated in the claims. All patents, patent applications, and publications mentioned herein are incorporated by reference in their entireties.

What is claimed is:

1. A process for the preparation of N-aryl amine compounds, comprising reacting a compound having an amino group with an arylating compound in the presence of a base and a transition metal catalyst under reaction conditions effective to form an N-aryl amine compound, said transition metal catalyst comprising a Group 8 metal and at least one chelating ligand selected from the group consisting of bisphosphines having at least one stearically hindered alkyl substituent.

2. The process of claim 1, wherein said compound having an amino group is selected from the group consisting of primary amines, secondary amines, and combinations thereof.

3. The process of claim 2, wherein said primary amine is selected from the group consisting of NH$_2$Ph, NH$_2$Bu, and combinations thereof.

4. The process of claim 2, wherein said secondary amine is selected from the group consisting of morpholine, piperidine, and combinations thereof.

5. The process of claim 1, wherein said arylating compound is selected from those having the formula

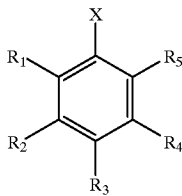

wherein X is a halogen atom or a sulfur-containing leaving group, and R$_1$, R$_2$, R$_3$, R$_4$, R$_5$ are independently selected from the group consisting of H, CN, alkyl, alkoxy, vinyl, alkenyl, formyl, CF$_3$, CCl$_3$, halide, C$_6$H$_5$, amide, acyl, ester, alkoxy, amino, thioalkoxy, phosphino, and combinations thereof.

6. The process of claim 1 wherein said arylating compound is selected from the group consisting of heterocyclic compounds, aryl phosphates, aryl trifluoroacetates, and combinations thereof.

7. The process of claim 5, wherein said sulfur-containing leaving group is selected from the group consisting of sulfonate, triflate, tosylate, and combinations thereof.

8. The process of claim 5, wherein said arylating compound is selected from those having the formula ClC$_6$H$_4$R, wherein R is selected from the group consisting of p-CN, p-t-Bu, m-OMe, o-Me, p-C(O)H, p-CF$_3$, p-Ph, p-C(O)NEt$_2$, p-H, and p-C(O)Ph.

9. The process of claim 1, wherein said arylating compound is selected from the group consisting of aromatic and heteroaromatic halides.

10. The process of claim 9, wherein said arylating compound is selected from the group consisting of aromatic and heteroaromatic chlorides.

11. The process of claim 1, wherein said base is selected from the group consisting of alkali metal hydroxides, alkali metal alkoxides, metal carbonates, alkali metal amides, alkali metal aryl oxides, phosphates, tertiary amines, tetraalkylammonium hydroxides, diaza organic bases, and combinations thereof.

12. The process of claim 1, wherein said Group 8 metal is palladium, platinum, or nickel.

13. The process of claim 1, wherein said transition metal catalyst has the formula

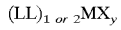

$(LL)_{1 \text{ or } 2}MX_y$ wherein (LL) is the chelating ligand, M is the Group 8 transition metal, each X is independently a monovalent or divalent anionic ligand, or a neutral dative ligand, and wherein y varies from 0 to 4.

14. The process of claim 1, wherein said bisphosphine having at least one stearically hindered alkyl substituent is a phosphinoferrocene selected from the group consisting of (R)-(−)1-[(S)-2-(dicyclohexylphosphino)ferrocenyl]ethyldicyclohexylphosphine, (R)-(−)1-[(S)-2-(diphenylphosphino)ferrocenyl]ethyldi-t-butylphosphine, and combinations thereof.

15. The process of claim 1, wherein said transition metal catalyst is prepared in situ in the reaction mixture.

16. The process of claim 15, wherein said transition metal catalyst is prepared from an alkene or diene complex of a Group 8 transition metal complex combined with (R)-(−)1-[(S)-2-(dicyclohexylphosphino)ferrocenyl]ethyldicyclohexylphosphine or (R)-(−)1-[(S)-2-(diphenylphosphino)ferrocenyl]ethyldi-t-butylphosphine.

17. The process of claim 16, wherein the alkene complex of the Group 8 transition metal is di(benzylidene)acetone.

18. The process of claim 1, wherein said transition metal catalyst is anchored or supported on a support.

19. The process of claim 1, wherein said reaction conditions further comprise a solvent selected from the group consisting of aromatic hydrocarbons, chlorinated aromatic hydrocarbons, ethers, water, aliphatic alcohols, and combinations thereof.

20. The process of claim 1, further comprising the step of isolating said N-aryl amine compounds.

21. A process for the preparation of N-aryl amine compounds, comprising reacting a primary amine compound with an arylating compound selected from the group consisting of aryl chlorides and aryl tosylates, in the presence of a base and a transition metal catalyst selected from the group consisting of (R)-(−)1-[(S)-2-(dicyclohexylphosphino)ferrocenyl]ethyldicyclohexylphosphine, (R)-(−)1-[(S)-2-(diphenylphosphino)ferrocenyl]ethyldi-t-butylphosphine, and combinations thereof, under reaction conditions effective to form an N-arylated amine compound.

* * * * *